(12) United States Patent
Sitton

(10) Patent No.: US 11,320,424 B2
(45) Date of Patent: May 3, 2022

(54) SPECIFIC BINDING CHEMILUMINESCENT ASSAY

(71) Applicant: 3M INNOVATIVE PROPERTIES COMPANY, St. Paul, MN (US)

(72) Inventor: Gregory W. Sitton, Minneapolis, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 17/258,568

(22) PCT Filed: Jul. 10, 2019

(86) PCT No.: PCT/IB2019/055895
§ 371 (c)(1),
(2) Date: Jan. 7, 2021

(87) PCT Pub. No.: WO2020/012390
PCT Pub. Date: Jan. 16, 2020

(65) Prior Publication Data
US 2021/0293795 A1    Sep. 23, 2021

Related U.S. Application Data

(60) Provisional application No. 62/697,521, filed on Jul. 13, 2018.

(51) Int. Cl.
*G01N 33/542* (2006.01)
(52) U.S. Cl.
CPC ................... *G01N 33/542* (2013.01)
(58) Field of Classification Search
CPC ...... C09B 15/00; G01N 21/76; G01N 21/763; G01N 33/542; G01N 33/582; G01N 33/536; C12Q 1/28
See application file for complete search history.

(56) References Cited

U.S. PATENT DOCUMENTS

| | | | |
|---|---|---|---|
| 4,837,395 A | 6/1989 | Leeder | |
| 5,089,383 A | 2/1992 | Leeder | |
| 5,171,668 A | 12/1992 | Sugiyama | |
| 5,206,149 A | 4/1993 | Oyama | |
| 5,324,835 A | 6/1994 | Yamaguchi | |
| 5,420,275 A | 5/1995 | Masuya | |
| 5,491,072 A | 2/1996 | Akhavan-Tafti | |
| 5,497,072 A | 3/1996 | LeComte | |
| 5,512,451 A | 4/1996 | Kricka | |
| 5,523,212 A | 6/1996 | Akhavan-Tafti | |
| 5,593,845 A | 1/1997 | Akhavan-Tafti | |
| 5,922,558 A | 7/1999 | Akhavan-Tafti | |
| 6,030,803 A | 2/2000 | Jacquemijns | |
| 6,406,913 B1 | 6/2002 | Ullman | |
| 6,696,569 B2 | 2/2004 | Akhavan-Tafti | |
| 6,891,057 B2 | 5/2005 | Akhavan-Tafti | |
| 6,911,305 B2 | 6/2005 | Levison | |
| 7,732,153 B2 | 6/2010 | Akhavan Tafti | |
| 9,029,092 B2 | 5/2015 | Akhavan Tafti | |
| 10,718,003 B2 * | 7/2020 | Rey | C12Q 1/14 |
| 2007/0172878 A1 | 7/2007 | Akhavan-Tafti | |
| 2007/0264664 A1 | 11/2007 | Akhavan-Tafti | |
| 2007/0264665 A1 | 11/2007 | Akhavan-Tafti | |
| 2010/0267071 A1 | 10/2010 | Akhavan-Tafti | |
| 2013/0084652 A1 | 4/2013 | Shapir | |
| 2015/0323541 A1 | 11/2015 | Liu | |
| 2017/0191111 A1* | 7/2017 | Rey | C12Q 1/14 |

FOREIGN PATENT DOCUMENTS

| | | |
|---|---|---|
| JP | 61-264262 | 11/1986 |
| JP | 2002-524102 | 8/2002 |
| WO | WO 1991-019979 | 12/1991 |
| WO | WO 2000-015618 | 3/2000 |
| WO | WO 2007-058654 | 5/2007 |
| WO | WO 2007-133988 | 11/2007 |
| WO | WO 2007-134098 | 11/2007 |
| WO | WO 2010-099479 | 9/2010 |
| WO | WO 2010-099486 | 9/2010 |
| WO | WO 2020/012391 | * 1/2020 |

OTHER PUBLICATIONS

"Cortisol Sparcl Assay", Life Diagnostics, Catalog No. CORT-SP, 3 pages.
Akhavan Tafti, "A homogeneous chemiluminescent immunoassay method", Journal of the American Chemical Society, 2013, vol. 135, No. 11, pp. 4191-4194.
Ci, "The Use of Mn-TPPS4 Mimetic Peroxidase in a DNA Hybridization Assay", Microchemical Journal, 1995, vol. 52, pp. 257-262.
Horton, "Enzyme immunoassays for the estimation of adenosine 3',5' cyclic monophosphate and guanosine 3',5' cyclic monophosphate in biological fluids", J Immunological Methods, 1992, vol. 155, pp. 31-40.
Ji, "Bifunctional Reagents," Methods in Enzymology,1983, vol. 91, pp. 580-609.
Martinello, "Mechanism of ascorbic acid interference in biochemical tests that use peroxide and peroxidase to generate chromophore",2006, Clinica Chimica Acta, vol. 373, pp. 108-116.
Tyrrell; "Development of a micro-fluidic manifold for copper monitoring utilizing chemiluminescence detection"; The Royal Society of Chemistry, 2004, vol. 4; pp. 384-390.
Veljovic-Jovanovic, "Are leaf hydrogen peroxide concentrations commonly overestimated? The potential influence of artefactual interference by tissue phenolics and ascorbate.", 2002, Plant Physiol. Biochem. vol. 40, pp. 501-507.
International Search report for PCT International Application No. PCT/IB2019/055895 dated Dec. 12, 2019, 4 pages.
Cinquanta et al., "Chemiluminescent immunoassay technology: what does it change in autoantibody detection?," 2017, *Autoimmun Highlights*, 8(9):1-8.

* cited by examiner

*Primary Examiner* — Galina M. Yakovleva
(74) *Attorney, Agent, or Firm* — 3M IPC

(57) ABSTRACT

Method of assaying for an analyte in a sample, and kits for performing the assay.

13 Claims, No Drawings

SPECIFIC BINDING CHEMILUMINESCENT ASSAY

CROSS REFERENCE TO RELATED APPLICATIONS

This application is a national stage filing under 35 U.S.C. 371 of PCT/IB2019/055895, filed 10 Jul. 2019, which claims the benefit of U.S. Provisional Application No. 62/697,521, filed 13 Jul. 2018, the disclosure of which are incorporated by reference in their entireties herein.

BACKGROUND

Solution phase luminescence assays are known, for example in WO2010099486. Known assays detect the presence or amount of a substance based on specific recognition and binding together of specific binding partners. For example, in immunoassays an antibody binds to a particular binding partner. As another example, in nucleic acid binding assays a nucleic acid strand, such as an aptamer, binds to a specific binding partner. Some assays use chemiluminescence to create a signal and relate that signal to the amount of analyte.

SUMMARY

A method of assaying for an analyte in a sample can comprise forming a reaction mixture and admixing a trigger solution and the reaction mixture. The analyte to be assayed for may be present in the sample, such that the assay can determine the presence or absence of the analyte, subject to the limit of detection of the assay.

The reaction mixture used in the assay is typically an aqueous solution comprising a chemiluminescent-labeled specific binding partner, wherein the chemiluminescent-labeled specific binding partner comprises a chemiluminescent label irreversibly bound to a first specific binding partner, and wherein the chemiluminescent-labeled specific bonding partner is capable of binding to the analyte to form an analyte-bound chemiluminescent labeled specific binding complex. The reaction mixture typically also comprises an activator-labeled specific binding partner, wherein the activator-labeled specific binding partner comprises an activator label irreversibly bound to a second specific binding partner. The reaction mixture typically further comprises a selective signal inhibiting agent.

The method further comprises measuring an analyte signal, and measuring a glow signal after measuring the analyte signal.

DETAILED DESCRIPTION

Throughout this disclosure, singular forms such as "a," "an," and "the" are often used for convenience; however, the singular forms are meant to include the plural unless the singular alone is explicitly specified or is clearly indicated by the context. When the singular alone is called for, the term "one and only one" is typically used.

Terms such as "common," "commonly," "typical," "typically," "usual," and "usually" are used to refer to features that are common, typical, or usual ways of making or practicing the invention(s) described herein. Those terms are not to be construed to mean that such features are present in the prior art, much less that they are common, typical, or usual, in the prior art.

Some terms in this disclosure are defined below. Other terms will be familiar to the person of skill in the art, and should be afforded the meaning that a person of ordinary skill in the art would have ascribed to them.

Analyte: a substance to be detected or quantified in an assay. One or more substances having a specific binding affinity to the analyte, and particularly one or more specific binding partners, are typically used in the assay to facilitate detection of an analyte. The analyte can be a protein, peptide, nucleotide, nucleoside, antibody, hapten, small molecule (i.e., non-polymeric molecule), or the like to which a specific binding partner can bind. Exemplary analytes include not only drugs such as steroids, hormones, proteins, glycoproteins, mucoproteins, nucleoproteins, phosphoproteins, opioids, vitamins, antibacterials, antifungals, antivirals, purines, antineoplastic agents, amphetamine, azepines, prosteglandins, as well as metabolites of drugs, but also nucleosides, organonucleosides, nucleotides, organonucleotides, ribosides, DNA, DNA segments, RNA, RNA segments, PDNA, PDNA segments, aptamers, toxins such as hemotoxins, phototoxins, neurotoxins, cyanotoxins, dinotoxins, necrotoxins, myotoxins, mycotoxins, such as T-2 mycotoxin, aflatoxins, botulism toxin, ricin, apitoxin, and other environmental toxins or biotoxins. Analytes can also be cells, viruses, bacteria, or fungi.

Activator: a compound that effects the activation of a chemiluminescent compound so that, in the presence of a trigger, the chemiluminescent compound luminesces.

Activator-labeled specific binding partner: a reactant that includes a specific binding member for an analyte and an activator directly or indirectly (e.g., through a linker) bound to the specific binding partner.

Chemiluminescent compound: a compound that undergoes a reaction causing the emission of light, for example by being converted into another compound formed in an electronically excited state or by being converted to an electronically excited state and then relaxing into a ground state. The excited state can be a single or triplet excited state. The excited state may emit light directly upon relaxation to the ground state, or may first transfer energy, such as by a Forester or Dexter mechanism, to an energy acceptor that in turn emits light.

Chemiluminescent-labeled specific binding partner: a reactant that includes a specific binding member for an analyte and a chemiluminescent compound directly or indirectly (e.g., through a linker) bound to the specific binding partner.

Analyte signal: a signal, such as a chemiluminescent output from an assay, that relates to the amount of analyte present in a sample. When the analyte signal is chemiluminescent output, it can be measured as the luminescence intensity at a designated wavelength or as the integral of luminescence over a period of time.

Glow signal: a signal, such as a chemiluminescent output, that occurs after all of the selective signal reducing agent has been consumed such that the selective signal reducing agent no longer reduces the signal in the assay.

Background signal: a signal, such as a chemiluminescent output, that does not relate to the amount of analyte present in a sample.

Irreversible bond: a bond associating two moieties, typically a specific binding partner and a chemiluminescent label or a specific binding partner and an activator label, that is not broken while performing the assays described herein. An irreversible bond may be broken by some other means, such as the use of chemical compounds or under physical conditions such as temperature, that the bond is not exposed to during the assays described herein. Typical bonds that may be irreversible bonds include covalent bonds, ionic bonds, and the like. Two moieties that are connected by an irreversible bond are said to be "irreversibly bound." An irreversible bond is distinguished from a reversible binding interaction, such as the reversible binding of specific bonding partners or of an analyte to a specific bonding partner.

Prior art chemiluminescence based-assays binding assays, such as the immunoassays described in US20100267071, as well as other assays such as those based on aptamer binding, etc., compare the chemiluminescence signal of a test sample with unknown concentration of analyte with a standard curve that is generated by using a plurality of samples with known concentration of analyte.

In a specific chemiluminescent assay, as described for example in US20100267071, a test sample containing an unknown concentration of analyte is admixed with an assay solution containing a chemiluminescent-labeled specific binding partner, an activator-labeled specific binding partner, and a selective signal inhibiting agent to form a reaction mixture. A trigger solution is then admixed with the reaction mixture. The trigger solution contains an oxidation or reducing agent, typically a peroxide, and in many cases an enhancer.

The assay proceeds in one of two formats. In a "competitive assay" format, the activator-labeled specific binding partner binds to the chemiluminescent-labeled specific binding partner in a complex that may be pre-formed or may form in situ. When analyte is present, the analyte and the chemiluminescent-labeled specific binding partner compete to bind the chemiluminescent-labeled specific binding partner. In the presence of a trigger solution, the chemiluminescent label on chemiluminescent-labeled specific binding partner that is bound to activator-labeled specific is in operable proximity to, and is therefore activated by, the activator-labeled specific binding partner causing luminescence. Chemiluminescent-labeled specific binding partner that is bound to analyte is not in operable proximity to the activator-labeled specific binding partner, and therefore its chemiluminescent label is not activated and it does not luminesce. In this format, the analyte signal is the luminescence intensity and it is inversely related to the analyte concentration.

An alternative is a "sandwich assay" format whereby the activator-labeled specific binding partner and the chemiluminescent-labeled specific binding partner both bind with the analyte, typically on different portions of the analyte, to bring the chemiluminescent label in operable proximity with the activator-labeled binding partner. The chemiluminescent label of the chemiluminescent-labeled specific binding partner in the resulting "sandwich" complex is in operable proximity to the activator-labeled specific binding partner and therefore luminesces. In the absence of analyte, the activator-labeled binding partner is not in operable proximity to the activator-labeled specific binding partner and therefore does not luminesce. In this format, the analyte signal is the luminescence intensity and it is directly related to the analyte concentration.

In either case, the intensity of the analyte signal in the test sample is measured in a luminometer and compared to a standard curve of luminescence intensity vs. concentration that is constructed by performing the same assay with standard samples having known concentrations of analyte. Correlating the analyte signal to the standard curve then provides a concentration of the analyte.

While this may be acceptable when the sample being analyzed contains only analyte and water, most commercial applications of chemiluminescence will also contain other substances besides the analyte. For example, when a test sample from a food substance is being assayed for the presence of a toxin, then many chemical compounds, such residual compounds from the food substance, will generally be present in addition to the toxin. These other compounds can interfere with the production of analyte signal, typically by interfering with the oxidation or reduction reactions that produces the chemiluminescent species. In this case, the correlation of the analyte signal to the standard curve will not provide an accurate concentration of the analyte in the test sample because the standard curve will be generated from solutions that do not contain these other interfering compounds. This results in a correlation error wherein the comparing the analyte signal to the standard curve does not accurately provide the concentration of the analyte in the test sample. For example, one selective signal inhibiting agent that can be used is ascorbic acid, which is also found in many food substances either naturally or as an added antioxidant. If a significant amount of ascorbic acid is present in the test sample, then it can further inhibit production of the analyte signal from the test sample and the concentration obtained by correlation of the analyte signal to the standard curve can be too low. This can be a significant problem, particularly when a harmful food contaminant is being assayed for, because the assay can incorrectly suggest that a food has safe levels of contaminant when in fact the food has unsafe levels of contaminant.

More generally, the errors in analyte concentration that can result from the interference of other compounds in the sample being assayed can be significant, in some cases as much as 40% or even greater. In the example of analyzing a food sample for toxins, some toxins are unsafe for animal consumption at levels as low as 5 ppb or even lower. Thus, these errors can mean the difference between, on the one hand, discarding a food sample that is in fact safe to consume, or on the other hand providing the false belief that a toxin is present at a safe level when in fact it is present at an unsafe level that may cause illness or death in an animal that consumes it.

Prior art solutions to this problem have not been acceptable. Removing compounds other than the analyte from the test sample to prevent interference with binding is exceptionally difficult and impractical, if not impossible, to achieve in a commercial setting, where thousands, tens of thousands, or even more different compounds of unknown identity may be present in the test sample. Another unacceptable prior art solution is to significantly dilute the test sample to the point where interference of compounds other than the analyte is negligible. This solution is unacceptable because the analyte concentration is also diluted and therefore the lowest level of detection ("LLD") and lowest level of quantification (LLQ) of the analyte is reduced. As indicated above, the concentration of many relevant analytes needs to be determined to the ppb levels, so the reductions in LLQ and LLD make a solution involving substantial dilution of the test sample unacceptable.

Not only should an acceptable solution avoid the aforementioned shortcomings, that is, it should be practical to use in a commercial setting and not require significant dilution of the test sample, but it should also be workable with a variety of binding agents, meaning that the technology should not depend on the nature of the binding partner (e.g., antibody, aptamer, etc.) such that it can be applied to a variety of different types of binding assays.

The present disclosure provides such a technical solution. Briefly, the technical solution, which is described in more detail below, involves observing the signal of the chemiluminescent-labeled specific binding partner after the signal from the analyte is no longer visible and after the selective signal inhibiting agent has been fully oxidized or reduced such that the selective signal inhibiting agent no longer inhibits the signal of unbound chemiluminescent labeled selective binding agent, referred to in this disclosure as the "glow signal." A calibration curve is constructed by determining the analyte signal and glow signal at known concentrations of analyte, and plotting the known concentrations of analyte against the formula: analyte signal/(glow signal+analyte signal). When measuring the sample, the analyte signal and glow signal are measured, the value of analyte signal/(glow signal+analyte signal) calculated for the sample, and then the calculated value is compared to the calibration curve in order to obtain the analyte concentration in the sample.

Specific Binding Partners

Two labeled specific binding partners are employed: one is activator-labeled and the other is chemiluminescent-labeled. Each of the specific binding partners is a molecule, usually a biological molecule, with a specific affinity for another substance. Examples include DNA, RNA, oligonucleotides, aptamers, antigens, antibodies, antibody-DNA chimeras, haptens, proteins, peptides, lectins, avidin, streptavidin, and biotin.

Each specific binding partner is generally non-identical to the other partner in that the two specific binding partners do not compete for the same or overlapping binding site on an analyte. For a typical case where the specific binding partner portion of both the activator-labeled specific binding partner and the chemiluminescent-labeled specific binding partner are antibodies, each of the antibodies has a different, non-competing epitope on the analyte.

Examples of specific binding partners that may be used in combination, that is, one can have a chemiluminescent label and the other can have an activator label, include complimentary oligonucleotides or polynucleotides, such as DNA, RNA, aptamers, and the like, avidin-biotin, streptavidin-biotin, hormone-receptor, lectin-carbohydrate, IG protein A-binding protein receptor, nucleic acid-nucleic acid binding protein, aptamer-aptamer, and nucleic acid-anti nucleic acid antibody. The specific binding partners discussed in US20100267071 are suitable.

Any of these can be adapted for a competitive assay format or a sandwich assay format. The identity of the specific binding partners determines the format of the assay, specifically, whether the assay is a sandwich assay or a competitive assay. In either case, the specific binding partner used for the chemiluminescent-labeled specific binding partner is selected to specifically bind analyte. Most commonly an antibody is used but any of the specific binding partners discussed above can also be employed. To adapt for a competitive assay format, the activator-labeled specific binding partner is designed as an activator-analyte analog conjugate. In this case, the activator is conjugated, directly or by way of a linker comprising an auxiliary substance as discussed herein, to an analog of the analyte, which may be the analyte itself or a compound with sufficient structural similarity to the analyte that it also binds to the chemiluminescent-labeled specific binding partner in essentially the same manner as the analyte.

To adapt for a sandwich assay format, both the chemiluminescent-labeled specific binding partner and the activator-labeled specific binding partner specifically bind to the analyte. In this case, the specific binding partner used for the activator-labeled specific binding partner is typically an antibody, but it may also be an aptamer or any of the specific binding partners discussed above. In this case, both the chemiluminescent-labeled specific binding partner and the activator-labeled specific binding partner bind to the analyte, typically to different binding sites on the analyte.

Both competitive and sandwich assays are known in the art, and the methods for accomplishing these adaptations are known. Examples and additional details regarding the assay formats and the specific binding partners can be found in US20100267071.

Chemiluminescent-Labeled Specific Binding Partner

The chemiluminescent-labeled specific binding partner is typically present in the reaction mixture at a concentration of less than $10^{-4}$ M, particularly less than $10^{-6}$ M, and most particularly $10^{-11}$ M to $10^{-7}$ M.

The chemiluminescent-labeled specific binding partner includes a specific binding partner that is labeled, usually by way of an irreversible bond, with a chemiluminescent label. Typically, each molecule of specific binding partner has at least one chemiluminescent label irreversibly bound thereto. In some cases, there may be as many as $10^2$ or even more chemiluminescent labels bound to each specific binding partner. It is not necessary that each specific binding partner molecule has the same number of chemiluminescent labels.

One or more chemiluminescent labels can be any suitable chemiluminescent moiety that can be bound, typically by way of an irreversible bond, to the specific bonding partner. The bond, typically irreversible bond, can be a direct connection or an indirect connection. In a direct connection, the one or more chemiluminescent labels are connected directly to the specific bonding partner without the use of a linker or auxiliary substance between the one or more chemiluminescent labels and the specific bonding partner. Direct connections are typically by way of an irreversible bond, such as an ionic bond, covalent bond, hydrophobic interaction, hydrogen bond, or the like, and most often a covalent bond.

When an indirect connection is employed, a linker, sometimes referred to in the art as an auxiliary substance, is used to connect the one or more chemiluminescent labels and the specific bonding partner. Any suitable linker can be used; suitable linkers will not prevent the one or more chemiluminescent labels from luminescing, and typically will not make the chemiluminescent-labeled specific binding partner insoluble in aqueous media. Exemplary linkers include proteins, such as streptavidin, avidin, neutravidin, biotin, cationized BSA, fos, jun, keyhole hemocyanin, immunoglobulins (including fragments or portions thereof), liposomes, micelles, synthetic dendrimers such as AMAM, synthetic polymers such as polyacrylic acid, natural polymers such as polysaccharides, for example functionalized dextran, polynucleotides, aptamers, and oligonucleotides, and the like. Polysaccharides, particularly amino-dextran or carboxyl-dextran, and self-assembling proteins, are most commonly employed.

The chemiluminescent label is formed by reacting a compound of the general formula CL-L-RG, wherein CL represents a chemiluminescent moiety, L represents a linker or covalent bond, and RG represents a reactive group, with a specific binding partner. Once the reaction is complete, the chemiluminescent moiety becomes a chemiluminescent label on the chemiluminescent-labeled specific binding partner. The chemiluminescent label reacts with the oxidation or reducing agent in the trigger solution or with the activator label in the activator-labeled specific binding partner to form an activated chemiluminescent compound, which is typically an excited state of the chemiluminescent label. The excited state can be either a singlet or triplet excited state.

The excited state can either relax with luminescence or it can undergo energy transfer to an emissive energy acceptor which in turn luminesces. In particular embodiments, the luminescence occurs very rapidly after addition of the trigger solution, more particularly reaching peak intensity within 2 seconds of the addition of the trigger solution. However, this is not required because a slower reaction can also give accurate results so long as the analyte signal is measured over a sufficient period of time.

A wide variety of chemiluminescent compounds that are suitable for binding to a specific binding partner, such as an antibody or antibody fragment, are known in the art. Any of these can be employed in the assays described herein.

Exemplary chemiluminescent moieties and chemiluminescent labels include aromatic cyclic diacylhydrazines such as luminol, isoluminol, aminobutylethylisoluminol, aminohexylethylisoluminol, 7-dimethylaminonaphthalene-1,2-dicarboxcylic acid hydrazine, ring substituted aminophthalhydrazides, anthracene-2,3-dicarboxylic acid hydrazides, phenanthrecene-1,2-dicarboxylic acid hydrazides, pyrenedicarboxylic acid hydrazides, 5-hydroxyphthalhydrazide, 6-hydroxyphthalhydrazide, xanthene dyes such as fluorescein, eosin, rhodamine dyes, rhodol dyes, chemiluminescent aromatic amines or heterocyclic amines, MCLA, indole acetic acid, isobutyraldehyde, trihydroxyaromatic compounds such as pyrogallol, phloroglucinol, and purpurogallin, as well as the phthalazinedione compounds disclosed in U.S. Pat. Nos. 5,420,275 and 5,324,835, acridan ketenedithioacetal compounds, and combinations of the foregoing. While any of these labels may be used either with or without an emissive energy acceptor, isobutyraldehyde is most often used with an emissive energy acceptor.

Some chemiluminescent labels can be labels of the Formula I:

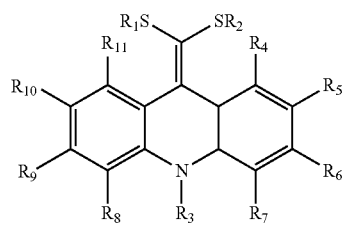

In labels of Formula I, each of $R_1$ and $R_2$ is independently H or an organic moiety containing from 1-50 atoms selected from C, N, O, S, P, Si, and halogen, plus sufficient hydrogen atoms to satisfy the valences of the non-hydrogen atoms. Most commonly, each of $R_1$ and $R_2$ is independently a linker to the specific binding partner, H, alkyl, substituted alkyl, alkenyl, substituted alkenyl, alkynyl, substituted alkynyl, aryl, substituted aryl, aralkyl, or substituted aralkyl. When $R_1$ and $R_2$ is substituted, it is most commonly substituted with 1-3 radicals selected from carbonyl, carboxyl, tri(alkyl)silyl, glycosyl, —SO$_3$—, —OSO$_3$—, —PO$_3$—, —OPO$_3$—, halogen, hydroxy, thiol, amino, quaternary ammonium, and quaternary phosphonium.

In labels of Formula I, $R_3$ is an H or an organic moiety containing from 1-50 atoms, most commonly from 1-20 atoms, selected from C, N, O, S, P, Si, and halogen, plus sufficient hydrogen atoms to satisfy the valences of the non-hydrogen atoms. Most commonly, $R_3$ is a linker to the specific binding partner, H, alkyl, substituted alkyl, alkenyl, substituted alkenyl, alkynyl, substituted alkynyl, aryl, substituted aryl, aralkyl, or substituted aralkyl. In such cases, $R_3$ most often has 1-20 carbon atoms. In many cases, $R_3$ is alkyl having from 1 to 4 carbon atoms, phenyl, benzyl, substituted benzyl, alkoxyalkyl, carboxyalkyl, or alkylsulfonic acid. It is possible that $R_3$, particularly when it is alkyl, substituted alkyl, alkenyl, or substituted alkenyl, but also in other cases, is covalently bound to $R_7$ or $R_8$ to form a ring, typically a five or six membered ring. When one or more of the above-mentioned moieties are substituted, it is most commonly substituted with 1-3 radicals selected from carbonyl, carboxyl, tri(alkyl)silyl, glycosyl—SO$_3$—, —OSO$_3$—, —OP$_3$—, —OPO$_3$—, halogen, hydroxy, thiol, amino, quaternary ammonium, and quaternary phosphonium.

In labels Formula I, each of $R_4$-$R_{11}$ is independently H or an organic moiety containing from 1-50 atoms selected from C, N, O, S, P, Si, and halogen, plus sufficient hydrogen atoms to satisfy the valences of the non-hydrogen atoms. Most commonly, each of $R_1$ and $R_2$ is independently a linker to the specific binding partner, H, alkyl, substituted alkyl, alkenyl, substituted alkenyl, alkynyl, substituted alkynyl, aryl, substituted aryl, aralkyl, substituted aralkyl, alkoxy, aryloxy, halogen, amino, substituted amine, carboxyl, carboalkoxy, carboxyamide, cyano, or sulfonate. Pairs of proximal $R_4$-$R_{11}$ moieties, such as $R_4$ and $R_5$, $R_8$ and $R_9$, etc. can be covalently bound to form a ring. In this case, the ring is typically a five to seven membered ring and most typically a five or six membered ring. The ring can be carbocyclic or heterocyclic, and in the latter case can contain herteroatoms such as N, O, or S, and can be unsubstituted or substituted either on one or more carbon atoms or one or more heteroatoms. When one or more of the above-mentioned moieties are substituted, it is most commonly substituted with 1-3 radicals selected from carbonyl, carboxyl, tri(alkyl)silyl, glycosyl, —SO$_3$—, —OSO$_3$—, —PO$_3$—, —OPO$_3$—, halogen, hydroxy, thiol, amino, quaternary ammonium, and quaternary phosphonium.

Most commonly, in Formula I, each of $R_4$-$R_{11}$ H.

Most commonly, the labels of Formula I that are employed are labels of Formula II

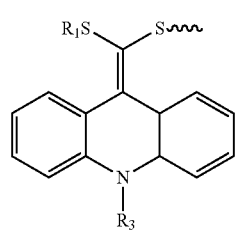

wherein the wavy line indicates the point of attachment to the specific binding partner. In such cases, $R_3$ is typically H, alkyl, substituted alkyl, alkenyl, substituted alkenyl, alkynyl, substituted alkynyl, aryl, substituted aryl, aralkyl, or substituted aralkyl. In such cases, $R_3$ most often has 1-20 carbon atoms, particularly alkyl having from 1 to 4 carbon atoms, phenyl, benzyl, substituted benzyl, alkoxyalkyl, carboxyalkyl, or alkylsulfonic acid. When one or more of the above-mentioned moieties are substituted, it is most commonly substituted with 1-3 radicals selected from carbonyl, carboxyl, tri(alkyl)silyl, glycosyl, —SO$_3$—, —OSO$_3$—, —PO$_3$—, —OPO$_3$—, halogen, hydroxy, thiol, amino, quaternary ammonium, and quaternary phosphonium.

In particular labels of Formula II, the wavy line designates the site of attachment to the specific binding partner or to a linker connecting the compound to the specific binding partner, $R^1$ and $R^2$ are independently selected from substituted alkyl, unsubstituted alkyl, substituted alkyenyl, unsubstituted alkenyl, substituted alkynyl, unsubstituted alkynyl, substituted aralkyl, and unsubstituted aralkyl, wherein when $R^1$ or $R^2$ is substituted it is substituted with 1-3 substituents, each substituent independently selected from carbonyl, carboxyl, trialkylsilyl, $—SO_3$, glycosyl, $—PO_3$, halogen, hydroxyl, thiol, amino, $C(O)NHNH_2$, quaternary ammonium, and quaternary phosphonium, and $R^3$ is selected from substituted alkyl, unsubstituted alkyl, substituted alkyenyl, unsubstituted alkenyl, substituted alkynyl, unsubstituted alkynyl, substituted aralkyl, and unsubstituted aralkyl, wherein when $R^1$ or $R^2$ is substituted it is substituted with 1-3 substituents, each substituent independently selected from carbonyl, carboxyl, trialkylsilyl, $—SO_3$, glycosyl, $—PO_3$, halogen, hydroxyl, thiol, amino, $C(O)NHNH_2$, quaternary ammonium, and quaternary phosphonium.

Labels of Formula II are bound to the specific binding partner by reaction of the specific binding partner with a compound of Formula III.

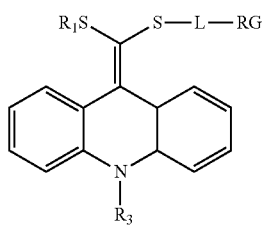

III wherein L and RG are as described above.

Examples of compounds of Formula III that can be employed are provided in Table 8 of US20100267071. Compounds of Formula I generally, and Formula III specifically, can be prepared according to methods disclosed in US20070172878. For example, a commercially available acridan or N-substituted acridan can be treated with strong base followed by carbon disulfide to form an acridan dithiocarboxylate, which is in turn esterified or partially esterified by conventional esterification methods to install substituent $R_1$. $R_2$ can be added by deprotonation of the remaining thiol with a strong base such as butyl lithium or sodium hydride and then treated with an appropriate electrophile to attach $R_2$. The substituents $R_1$ and $R_2$ may undergo further reactions to manipulate the functional groups thereon in order to achieve the desired compound of Formula III.

The chemiluminescent label can also be selected from aromatic cyclic dialhydrazides, trihydroxyaromatic compounds, acridan ketenedithioacetal compounds, acridan esters, acridan thioesters, acridan enols, and compounds having the formula

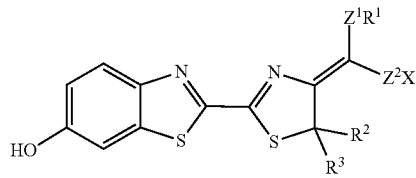

wherein
$R^1$ is selected from alyl, alkenyl, alkynyl, aryl, and aralkyl groups of 1-20- carbons or any of the foregoing substituted with 1-3 groups moieties that are independently selected from carbonyl, trialkyl silyl, $SO_3—$, $—OSO_3$, glycosyl, $PO_3—$, $—OPO_3$, halogen, hydroxyl, thiol, amino, quaternary ammonium, or quaternary phosphonium, X is selected from C1-C8 alkyl, aryl, aralkyl, alkyl or alkyl carbonyl having 1-20 carbon atoms, trialkyl silyl, $SO_3—$, glycosyl, and PO(OR')(OR") wherein R' and R" are independently selected from C1-C8 alkyl, cyanoalkyl, cyanoaryl, cyanoaralkyl, trialkylsilyl, alkali metal cation, alkaline earth cation, ammonium cation, and trianlkylphosphonium cation, $Z^1$ and $Z^2$ are independently selected from O and S atoms, and $R^2$ and $R^3$ are independently selected from H and C1-C8 alkyl.

Still further chemiluminescent labels are disclosed in U.S. Pat. Nos. 5,497,072, 523,212, 5,593,845, 5,922,588, 6,0130, 803, 6,696,569, 6,891,057, and US20100267071. Any of these or other chemiluminescent labels can be employed. Particularly suitable chemiluminescent labels and chemiluminescent-labeled specific binding partners include those disclosed in US20100267071.

Activator-Labeled Specific Binding Partner

The activator-labeled specific binding partner is typically present in the reaction mixture at a concentration of less than $10^{-4}$ M, particularly less than $10^{-6}$ M, and most particularly $10^{-11}$ M to $10^{-7}$ M.

The activator-labeled specific binding partner includes an activator label that is bound typically irreversibly bound, to a specific binding partner. Any suitable activator label can be used. A compound can be suitable to be an activator label when it meets two requirements. First, it can be able to accept or donate an electron, or in some rare cases multiple electrons, from or to the oxidation or reducing agent to form a radical, ion-radical, or, in uncommon cases, an ion. Such radical, ion-radical, or ion is sometimes referred to as an activated activator label, and the formation of an activated activator label is sometimes referred to as activating the activator label. Second, once an activated activator label is formed, it should be able to activate the chemiluminescent label on the chemiluminescent-labeled specific binding partner, and if applicable to the unbound chemiluminescent substrate, causing the chemiluminescent label, and if applicable the unbound chemiluminescent substrate, to luminesce.

Typical activator labels are peroxidases or compounds having peroxidase-like activity. Examples include lactoperoxidase, microperoxidase, myeloperoxidase, haloperoxidase, vanadium bromoperoxidase, horseradish peroxidase, fungal peroxidases, lignin peroxidase, Mn-dependent peroxidase, soybean peroxidases, and peroxidase mimetic compounds that are not enzymes but that have peroxidase-like activity such as Mn-TPPS4.

The activator-labeled specific binding partner can include conjugates or complexes of a peroxidase or compound having peroxidase-like activity with a biological molecule. In such cases, typical biological molecules that can be employed include DNA, RNA, aptamers, antibodies, antibody fragments, antibody-DNA chimeras, antigens, haptens, proteins, peptides, lechtins, avidin, streptavidin, and biotin.

One or more activator labels are bound, typically by way of an irreversible bond, to the specific bonding partner. The bond, typically irreversible bond, can be a direct connection or an indirect connection. In a direct connection, the one or more chemiluminescent labels are connected directly to the specific bonding partner without the use of a linker or auxiliary substance between the one or more chemiluminescent labels and the specific bonding partner. Direct connections are typically by way of an irreversible bond, such as an ionic bond, covalent bond, hydrophobic interaction, hydrogen bond, or the like, and most often a covalent bond.

When an indirect connection is employed, a linker, sometimes referred to in the art as an auxiliary substance, is used to connect the one or more chemiluminescent labels and the specific bonding partner. Any suitable linker can be used; suitable linkers will not prevent the one or more chemiluminescent labels from luminescing, and typically will not make the chemiluminescent-labeled specific binding partner insoluble in aqueous media. Exemplary linkers include proteins, such as streptavidin, avidin, neutravidin, biotin, cationized BSA, fos, jun, keyhole hemocyanin, immunoglobulins (including fragments or portions thereof), liposomes, micelles, synthetic dendrimers such as AMAM, synthetic polymers such as polyacrylic acid, natural polymers such as polysaccharides, for example functionalized dextran, polynucleotides, aptamers, and oligonucleotides, and the like. Polyasaccharides, particularly amino-dextran or carboxyl-dextran, and self-assembling proteins, are most commonly employed.

Suitable activator-labeled specific binding partners include those disclosed in US20100267071.

Selective Signal Inhibiting Agents

Selective signal inhibiting agents reduce the noise signal caused by excess chemiluminescent-labeled specific binding partner that is present in the reaction mixture but does not participate in the assay described herein. Their function is described in more detail in US20100267071.

Typically, one or more selective signal inhibiting agents are present in the reaction mixture at a concentration of $10^{-6}$ M to $10^{-1}$ M, most often $10^{-5}$ M to $10^{-4}$ M. Particular concentrations include $5 \times 10^{-6}$ M to $5 \times 10^{-4}$ M, and more particularly $5 \times 10^{-5}$ M to $5 \times 10^{-4}$ M.

Compounds that are suitable for use as selective signal inhibiting agents include anti-oxidants, particularly sacrificial anti-oxidants, as well as other molecules that can react with the radical, ion-radical, or in some cases ion, formed by the oxidation or reducing agent interacting with the activator label on the activator-labeled selective binding partner or, in some cases, the oxidation or reducing agent. Any anti-oxidant can be employed, because for the purposes of this disclosure the various options for selective signal inhibiting agents function in the same way. Specifically, the react with the oxidation or reducing agent, which is usually a peroxide, or with the activated activator label on the activator-labeled specific binding partner, to quench the peroxide radical or the activated activator label.

Some specific anti-oxidants that can be employed as selective signal inhibiting agents are described in US20100267071. Examples include glutathione, ascorbic acid, particularly L-ascorbic acid, salts of ascorbic acid, particularly salts of L-ascorbic acid, uric acid, L-ascorbic acid-6-palmitate, tocopherol, 5,6-isopropylidene-L-acobic acid, isoascorbic acid, including D-isoascorbic acid, L-isoasocrbic acid, or both, sodium sulfite, diethylhydroxylamine, BHT,

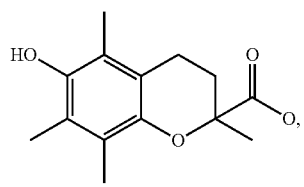

-continued

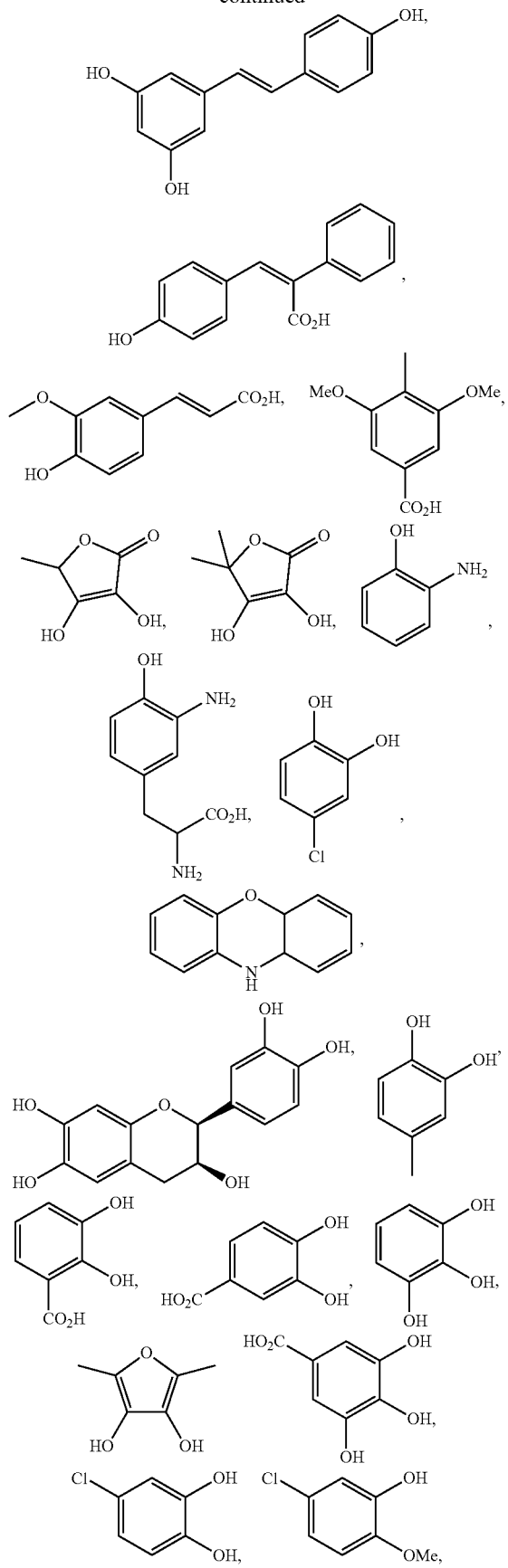

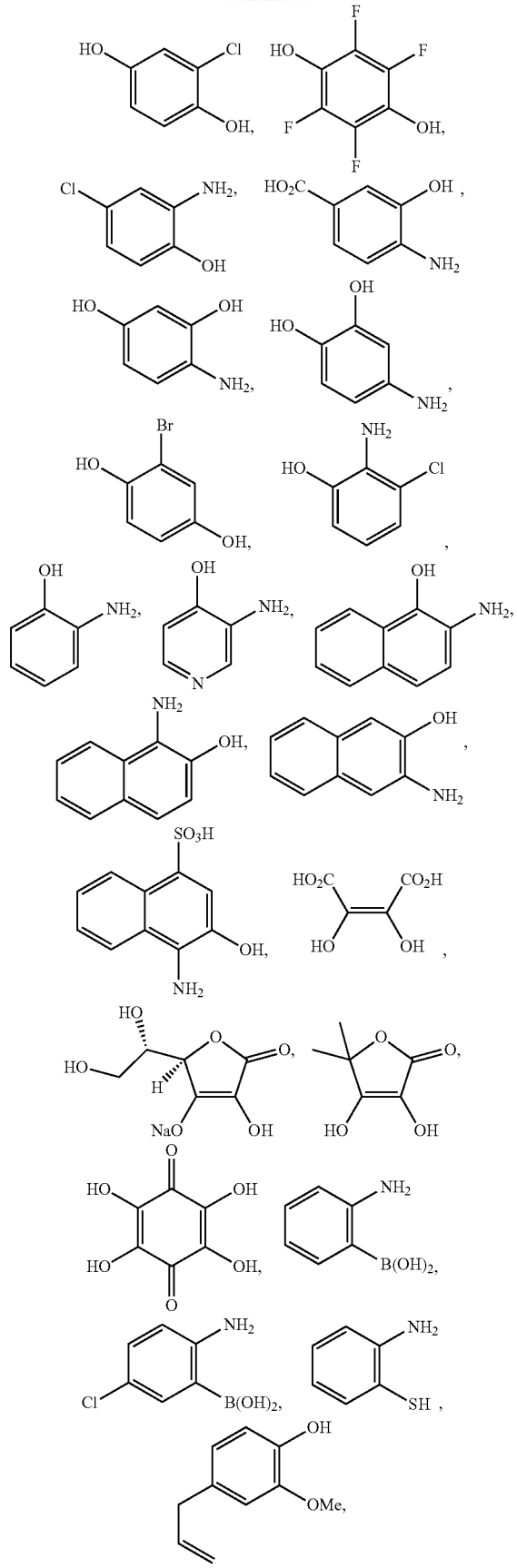

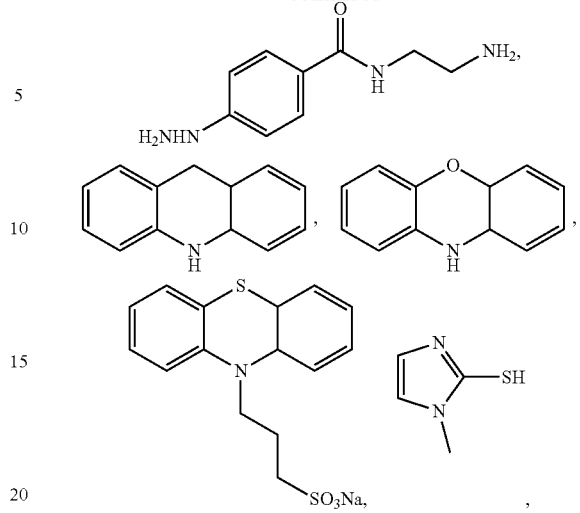

and combinations of the foregoing. Most commonly, tocopherol or ascorbic acid, and particularly ascorbic acid, is used.

In use, the one or more selective signal inhibiting agents can be provided in any suitable way. For example, they can be provided as a component of the trigger solution, in which case the reaction mixture is formed when the trigger solution is added. They can also be provided with one or both of the chemiluminescent-labeled specific binding partner or activator-labeled specific binding partner, or they can be added alone as a solid or as a solution of appropriate concentration. Most commonly, the one or more selective signal inhibiting agents are provided in a working solution at a concentration that is ten-fold higher, or in some cases even greater than ten-fold higher, than the concentration to be provided in the reaction mixture, particularly after addition of the trigger solution. The working solution is typically aqueous, and in many cases can be water, such as buffered water, but in some cases it can also contain surfactants, ethanol, glycols, and or the like in order to provide a sufficiently high concentration of the one or more selective signal inhibiting agents. In any event, they are added in an appropriate amount to achieve a suitable concentration in the reaction mixture.

Trigger Solution

The trigger solution provides one or more oxidation or reducing agents that are needed to cause luminescence from the chemiluminescent-labeled specific binding partner and, in some cases, from the background agent. The one or more oxidation or reducing agents may perform this function by reacting directly with the chemiluminescent label and, where applicable, the background agent, but more commonly the one or more oxidation or reducing agents react with the activator label on the activator-labeled specific binding partner to facilitate the action of the activator label with the chemiluminescent label.

The one or more oxidation or reducing agents can be any compounds that activate the activator label on the activator-labeled specific binding partner. Most commonly, the one or more oxidation or reducing agents are one or more peroxides that interact with the activator label, which typically is a peroxidase or a compound having peroxidase-like activity, to activate the activator label. While any peroxide that reacts with the peroxidase or a compound having peroxidase-like activity can be used, commonly used peroxides include alkyl peroxides, alkyl hydroperoxides, hydrogen peroxide, urea peroxide, carbamate peroxide, and perborates. The concentration of the peroxide can vary, but is typically from $10^{-8}$ M to 3 M, and most commonly $10^{-3}$ M to $10^{-1}$ M.

While not required, an enhancer is typically used as a component of the trigger solution. The enhancer can be any compound that promotes the reactivity of the activator label, typically a peroxidase enzyme, reduces noise signal in the assay, or both. Typical enhancers include phenolic compounds, aromatic amines, mixtures of phenoxazine or phenothizine with an indophenol or indoaniline, substituted hydroxybenzoxazoles, substituted or unsubstituted arylboronic acids as well as their esters and anhydrides, and the like. Some suitable enhancers are disclosed in US20100267071, U.S. Pat. Nos. 5,171,668, 5,206,149, and 5,512,451. When employed, an enhancer is typically present at a concentration of $10^{-5}$ M to $10^{-1}$ M As discussed above, the one or more selective signal inhibiting agents can be present in the trigger solution in addition to the oxidation or reducing agent and, when employed, the enhancer.

The trigger solution typically contains the various solutes described in an aqueous solvent. The aqueous solvent is typically buffered water. Any buffer useful with biological systems can be employed so long as it does not interfere with the luminescence of the chemiluminescent label or the assay to the point where a sufficient analyte signal cannot be produced. Most useful buffers will maintain a pH of 5 to 10.5. Particularly useful buffers maintain a pH of 6.0-9.0, such as 65.-8.5, and most particularly 7.0-8.0

Exemplary buffers that can be used are disclosed in US 20100267071. Most commonly, the buffer is selected from phosphate, borate, acetate, tris(hydroxy-methylamine)methane, glycine, tricine, 2-amino-2-methyl-1-propanol, diethanolamine, MOPS, HEPES, IVIES, and the like.

One or more detergents or polymeric surfactants can be used to enhance luminescence or decrease the noise signal. Examples include polyoxyethylenated alkyl phenols, polyoxyethhylenated alcohols, polyoxyethylenated ethers, polyoxyethylenated sorbitol esters, quaternary ammonium salts such as CTAB, and quaternary phosphonium salts. Particularly useful examples are polymeric cationic surfactants, most particularly quaternary ammonium salts and quaternary phosphonium salts.

As discussed above, the one or more selective signal inhibiting agents can optionally be present in the trigger solution.

As an example, a trigger solution can contain an aqueous buffer, a peroxide at a concentration of $10^{-5}$ M to 1 M, and an enhancer at a concentration of $10^{-5}$ M to $10^{-1}$ M. As another example, a trigger solution can contain an aqueous buffer, a peroxide at a concentration of $10^{-5}$ M to 1 M, an enhancer at a concentration of $10^{-5}$ M to $10^{-1}$ M, and one or more selective signal inhibiting agents at a concentration such that the one or more selective signal inhibiting agents has a concentration of $10^{-6}$ M to $10^{-1}$ M in the reaction mixture.

Signals

In either the competition format or the sandwich format, the analyte signal can be measured, for example, as a luminescence signal such as a fluorescence signal. Most commonly, the analyte signal is measurable almost immediately after the addition of the trigger solution. The duration of the analyte signal is typically only a brief period of time, such as twenty seconds or less, ten seconds or less, five seconds or less, three seconds or less, two seconds or less, or even one second or less after addition of the trigger solution. After that time, the analyte signal is no longer detectable. Immediately after the analyte signal is no longer detectable, the background signal is also typically not detectable, or barely detectable, because of the presence of the selective signal reducing agent.

As discussed above, the selective signal reducing agent is typically an oxidation agent or a reducing agent, and most commonly a reducing agent, that is sacrificially oxidized or reduced in order to reduce the background signal. Once all of the selective signal reducing agent is consumed by way of oxidation or reduction, the signal from the chemiluminescent labeled selective binding partner is no longer reduced, and a glow signal becomes detectable. Typically, the glow signal will become detectable after the analyte signal is no longer detectable, but still within a short time of the addition of the trigger solution. Depending on the duration of the analyte signal, in many cases the glow signal becomes detectable in two minutes or less, ninety seconds or less, seventy-five seconds or less, sixty seconds or less, forty-five seconds or less, thirty seconds or less, or even twenty seconds or less after the addition of the trigger solution. The glow signal is typically the same type of signal, most commonly luminescence and usually fluorescence, as the analyte signal, and therefore can be detected in the same manner as the analyte signal.

The time at which the glow signal becomes detectable can be adjusted in at least two ways. First, the concentration of selective signal reducing agent can be changed. Increasing the amount of selective signal reducing agent will increase the time that must pass before the glow signal can be measured, whereas decreasing the amount of selective signal reducing agent will decrease the amount of time before the glow signal can be measured. Second, the amount activator labeled specific binding partner can be adjusted. Increasing the amount of chemiluminescent labeled specific binding partner will decrease the amount of time that must pass before the glow signal can be measured, whereas decreasing the amount of chemiluminescent labeled specific binding partner will increase the amount of time that must pass before the glow signal can be measured.

Detection

The various signals, such as glow signal and analyte signal, can be detected by any art-known devices. The type of device can depend on the type of signal. When the signal is a luminescence signal, a luminometer or CCD camera is typically used. Other useful detectors include photographic film, x-ray film, scintillation counters, actinometers, transmittance detectors such as UV/Vis and IR detectors, and the like. Most commonly, detection is performed in a test tube or in multi-well plates in a luminometer or in front of a CCD camera. The use of multi-well plates and a CCD camera can be convenient because in that case it can be possible to perform assays and detection of a plurality of test samples and standard samples at the same time, each in different wells of the multi-well plate. Detection can be performed with any of the numerous commercially available or art-known luminometers, CCD cameras, etc.

The glow signal, analyte signal, or both, can be the intensity of the maximum wavelength of the respective signal ($\lambda_{max}$). Alternatively, the glow signal, analyte signal, or both can be the integral of spectral peaks associated with the glow fluorescence and analyte fluorescence.

Quantification

In prior art assays, such as those described in WO2010099486, the analyte signals of a plurality standard samples with known concentration of analyte are used to make a calibration curve. Quantification is achieved by comparing the analyte signal of the test sample to the calibration curve. The inventors have recognized for the first time that this prior art quantification is inadequate and can give a large amount of error, particularly when the sample is not highly dilute.

Accurate quantification can be achieved at lower levels of dilution by measuring the analyte signal and the glow signal of a plurality of standard samples with known concentrations of analyte. A calibration curve is created by measuring the analyte signal and the glow signal of the standard samples and plotting the analyte concentration against the formula: analyte signal/(glow signal+analyte signal).

To determine the analyte concentration in a sample with unknown analyte concentration, the analyte signal and test signal are measured, and then the quantity analyte signal/(glow signal+analyte signal) is compared to the calibration curve in order to determine the analyte concentration. This method can not only provide results that are more accurate than uncorrected methods that do not use the glow signal to make the calibration curve, but also, in some cases, can be more accurate than ELISA assays that are not highly diluted, particularly for samples with interfering compounds but also in samples where the analyte itself can quench analyte signal.

Uses

The assay as described herein can find use in a variety of systems. ELISA systems are one use, but also assays involving aptamer binding and other, non-immunogen specific binding partners can be employed following the guidance herein and the knowledge of the artisan. Examples include solution hybridization assays, DNA detection in Southern blotting, RNA detection in Northern blotting, DNA or RNA sequencing, DNA or RNA fingerprinting, colony hybridization, and plaque assays, all of which are known in the art. Any analyte for which at least one specific binding partner can be made can be analyzed. Examples include antigens, toxins, venoms, nucleic acids, nucleotides, polynucleotides, drugs, steroids, haptens, antibodies, peptides, peptide fragments, hormones, receptors, primers, small molecules, and the like.

List of Illustrative Embodiments

This list of embodiments is meant to aid in understanding particular aspects of the invention. It is not intended to be limiting.

1. A method of assaying for an analyte in a sample, the method comprising
forming a reaction mixture, and
admixing a trigger solution to the reaction mixture; wherein the analyte to be assayed for may be present in the sample, the reaction mixture an aqueous solution comprising
a chemiluminescent-labeled specific binding partner comprising a chemiluminescent label irreversibly bound to a first specific binding partner, the chemiluminescent-labeled specific bonding partner being capable of binding to the analyte to form an analyte-bound chemiluminescent labeled specific binding complex,
an activator-labeled specific binding partner comprising an activator label irreversibly bound to a second specific binding partner, and
a selective signal inhibiting agent; and wherein the method further comprises
measuring an analyte signal, and
measuring a glow signal after measuring the analyte signal.

2. The method of embodiment 1, wherein the reaction mixture further comprises an enhancer.

3. The method of embodiment 1, wherein the trigger solution further comprises an enhancer.

4. The method of any of the preceding embodiments, wherein the selective signal inhibiting agent causes the ratio of signal produced by reaction between the chemiluminescent-labeled specific binding partner and the activator labeled specific binding partner in a complex with the analyte to exceed the signal from reaction between the chemiluminescent-labeled specific binding partner and activator labeled specific binding partner when no complex with the analyte is present.

5. The method of any of the preceding embodiments, wherein the selective signal inhibiting agent is selected from the group consisting of aromatic compounds having at least two hydroxyl groups in an ortho or para orientation, aromatic compounds having at least one hydroxyl group and an amino group that is ortho or para to one or more of the at least one hydroxyl groups, compounds having at least two hydroxyl groups substituted on an ethyleneically unsaturated group, and nitrogen heterocyclic groups.

6. The method of any of the preceding embodiments, wherein the selective signal inhibiting agent is selected from the group consisting of ascorbic acid, isoascorbic acid, 6-hydroxy-2,5,7,8-tetramethylchroman-2-carboxylic acid, ascorbic acid 6-palmitate, 5,6-isopropylidiene-ascorbic acid, butylated hydroxy toluene, glutathione, uric acid, one or more tocopherols, and catechin.

7. The method of any of the preceding embodiments, wherein the selective signal inhibiting agent is ascorbic acid.

8. The method of any of the preceding embodiments, wherein the chemilumiescent-labeled specific binding partner comprises a chemiluminescent label connected directly or indirectly to a specific binding pair member, wherein the chemiluminescent label is selected from aromatic cyclic dialhydrazides, trihydroxyaromatic compounds, acridan ketenedithioacetal compounds, acridan esters, acridan thioesters, acridan enols, and compounds having the formula

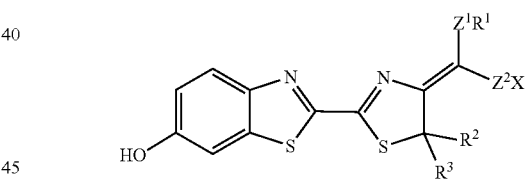

wherein
$R^1$ is selected from alyl, alkenyl, alkynyl, aryl, and aralkyl groups of 1-20- carbons or any of the foregoing substituted with 1-3 groups moieties that are independently selected from carbonyl, trialkyl silyl, $SO_3$—, —$OSO_3$, glycosyl, $PO_3$—, —$OPO_3$, halogen, hydroxyl, thiol, amino, quaternary ammonium, or quaternary phosphonium;
X is selected from C1-C8 alkyl, aryl, aralkyl, alkyl or alkyl carbonyl having 1-20 carbon atoms, trialkyl silyl, $SO_3$—, glycosyl, and PO(OR')(OR") wherein R' and R" are independently selected from C1-C8 alkyl, cyanoalkyl, cyanoaryl, cyanoaralkyl, trialkylsilyl, alkali metal cation, alkaline earth cation, ammonium cation, and trianlkylphosphonium cation;
$Z^1$ and $Z^2$ are independently selected from O and S atoms; and
$R^2$ and $R^3$ are independently selected from H and C1-C8 alkyl.

9. The method of any of embodiments 1-7 wherein the chemiluminescent-labeled specific binding partner comprises a chemiluminescent label connected directly or indirectly to a specific binding partner, wherein the chemiluminescent label has formula

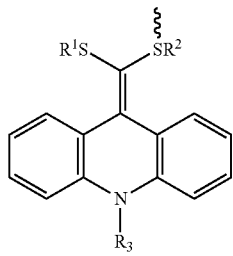

wherein
the wavy line designates the site of attachment to the specific binding partner or to a linker connecting the compound to the specific binding partner;
$R^1$ and $R^2$ are independently selected from substituted alkyl, unsubstituted alkyl, substituted alkyenyl, unsubstituted alkenyl, substituted alkynyl, unsubstituted alkynyl, substituted aralkyl, and unsubstituted aralkyl, wherein when $R^1$ or $R^2$ is substituted it is substituted with 1-3 substituents, each substituent independently selected from carbonyl, carboxyl, trialkylsilyl, —$SO_3$, glycosyl, —$PO_3$, halogen, hydroxyl, thiol, amino, $C(O)NHNH_2$, quaternary ammonium, and quaternary phosphonium;
$R^3$ is selected from substituted alkyl, unsubstituted alkyl, substituted alkyenyl, unsubstituted alkenyl, substituted alkynyl, unsubstituted alkynyl, substituted aralkyl, and unsubstituted aralkyl, wherein when $R^1$ or $R^2$ is substituted it is substituted with 1-3 substituents, each substituent independently selected from carbonyl, carboxyl, trialkylsilyl, —$SO_3$, glycosyl, —$PO_3$, halogen, hydroxyl, thiol, amino, $C(O)NHNH_2$, quaternary ammonium, and quaternary phosphonium.

10. The method of any of the preceding embodiments, wherein the activator-labeled specific binding partner comprises an activator label compound connected directly or indirectly to a specific binding pair member, wherein the activator label is selected from transition metal salts, transition metal complexes, and enzymes, and wherein the activator label has peroxidase activity.

11. The method of any of the preceding embodiments, wherein the activator label is a peroxidase enzyme.

12. The method of embodiment 11 wherein the activator label is horseradish peroxidase.

13. The method of any of the preceding embodiments, wherein at least one of the chemiluminescent-labeled specific binding partner and activator-labeled specific binding partner comprises an auxiliary substance selected from soluble proteins, streptavidin, avidin, neutravidin, biotin, cationized BSA, fos, jun, soluble synthetic dendrimer, soluble synthetic polymer, polysaccharide, dextran, organonuceotide, nucleotide, nucleoside, aptamer, liposome, and micelle.

14. The method of any of embodiments 2-12, wherein the enhancer is one or more compounds that promote the catalytic turnover of an activator having peroxidase activity.

15. The method of embodiment 13, wherein the enhancer is selected from phenol compounds, aromatic amines, benzoxazoles, hydroxybenzothiazoles, aryl boronic acids, and mixtures of any of the foregoing.

16. The method of any of the preceding embodiments, wherein the trigger solution comprises an oxidation or reducing agent.

17. The method of any of the preceding embodiments, wherein the trigger solution comprises a peroxide.

18. The method of embodiment 17, wherein the peroxide compound is selected from the group consisting of include alkyl peroxides, alkyl hydroperoxides, hydrogen peroxide, urea peroxide, carbamate peroxide, and perborates.

19. The method of embodiment 18, wherein the peroxide is hydrogen peroxide, alkyl peroxide, or alkyl hydrogen peroxide.

20. The method of any of the preceding embodiments, wherein the trigger solution comprises an enhancer selected from phenol compounds, aromatic amines, benzoxazoles, hydroxybenzothiazoles, aryl boronic acids, and mixtures of any of the foregoing.

21. The method of any of the preceding embodiments wherein all of the components of the trigger solution and the reaction mixture as well as the analyte are water soluble.

22. The method of any of the preceding embodiments wherein none of the trigger solution, the assay solution, or the reaction mixture contain a material that is conjugated directly or indirectly to a solid phase substance.

23. The method of any of the preceding embodiments, wherein the selective signal agent comprises a compound selected from the group consisting of aromatic compounds having at least two hydroxy moieties in an ortho or para orientation, aromatic compounds having a hydroxyl moiety and an amineo moiety in an ortho or para orientation, compounds having at least two vinyl hydroxyl groups, and nitrogen heterocycles.

24. The method of any of the preceding embodiments, wherein the selective signal inhibiting agent comprises ascorbic acid, and wherein the ascorbic acid is particularly L-ascorbic acid.

25. The method of any of the preceding embodiments, wherein the selective signal inhibiting agent comprises 6-hydroxy-2,5,7,8-tetramehtylchroman-2-carboxylic acid.

26. The method of any of the preceding embodiments, wherein the selective signal inhibiting agent comprises 2-amineophenol.

27. The method of any of the preceding embodiments, wherein the selective signal inhibiting agent comprises 3-amineo-tyrosine, particularly 3-amino-L-tyrosine.

28. The method of any of the preceding embodiments, wherein the selective signal inhibiting agent comprises 4-chlorocatechol.

29. The method of any of the preceding embodiments, wherein the selective signal inhibiting agent comprises phenoxazine.

30. The method of any of the preceding embodiments, wherein the selective signal inhibiting agent comprises 2-bromobenzne-1,4-diol.

31. The method of any of the preceding embodiments, wherein the selective signal inhibiting agent comprises 5,6-isopropylidine ascorbic acid.

32. The method of any of the preceding embodiments, wherein the selective signal inhibiting agent comprises 6-palmitate.

33. The method of any of the preceding embodiments, wherein the chemiluminescent-labeled specific binding partner and the activator-labeled specific binding partner each bind to the analyte in the sample.

34. The method of any of the preceding embodiments, wherein the chemiluminescent-labeled specific binding partner comprises a chemiluminescent labeled compound connected to an analog of the analyte and further wherein the analyte and the chemiluminescent-labeled specific binding partner compete to bind with the activator-labeled specific binding partner.

35. The method of any of the preceding embodiments, wherein the sample is a standard sample comprising a known concentration of analyte.

36. The method of embodiment 35, further comprising measuring the analyte signal and the glow signal from a plurality of standard samples comprising a known concentration of analyte.

37. The method of any of the preceding embodiments, comprising measuring the analyte signal and the glow signal from a test sample containing an unknown quantity of analyte.

38. The method of embodiment 36, further comprising preparing a calibration curve that compares the quotient of the analyte signal and the sum of the analyte signal and glow signal of the standard samples to the known concentration of analyte in the standard samples.

39. The method of embodiment 38, further comprising quantifying the amount of analyte in the test sample by comparing the quotient of the analyte signal and the sum of the analyte signal and glow signal from the test sample to a calibration curve.

40. The method of any of the preceding embodiments, wherein the analyte signal is a luminescence intensity or an area under the curve of a luminescence intensity.

41. The method of any of the preceding embodiments, wherein the glow signal is a luminescence intensity or an area under the curve of a luminescence intensity.

EXAMPLES

Materials

Ethylenediaminetetraacetic acid dipotassium salt (EDTA-dipotassium salt), para-Coumaric acid, TWEEN 20, Tris base, Tris hydrochloride, and Sodium ascorbate were obtained from the Sigma-Aldrich Corporation, St. Louis, Mo.

Hydrogen peroxide (30%, BAKER analyzed) was obtained from VWR International, Radnor, Pa.

Ethanol (200 proof) was obtained from Decon Labs Incorporated, King of Prussia, Pa.

PVP360 [poly(vinylpyrrolidinone) with an average molecular weight of 360,000] and PEG-6000 [poly(ethyleneglycol) with an average molecular weight of 6000] were obtained from the Sigma-Aldrich Corporation.

Aflatoxin B1 (AFB1) was obtained from the Sigma-Aldrich Corporation (catalog No. A6636).

Prior to use a 20 ppm (part per million) solution of AFB1 in methanol was prepared.

Surfactant A was prepared in PBS according to the solution formulation described in Table 1.

Phosphate buffered saline (PBS) was obtained from Thermo Fisher Scientific Incorporated, Waltham, Mass.

Surfactant B was prepared as a 3% solution (by volume) of MAKON-10 surfactant (Stepan Company, Northfield, Ill.) in PBS.

Anti-aflatoxin B1 monoclonal antibody (anti-AFB1) was obtained from Creative Diagnostics, Shirley, N.Y. (catalog No. DMAB2948).

The (anti-AFB1)-acridan [anti-AFB1 conjugated to acridan] was prepared by Life Diagnostics Incorporated, West Chester, Pa. and supplied as a 64 microgram/mL solution in stabilization buffer. Prior to use the (anti-AFB1)-acridan solution was diluted 1:10 (by volume) with PBS. AFB1-HRP [AFB1 conjugated to horseradish peroxidase (HRP)] was obtained from Creative Diagnostics as a 7.05 mg/mL solution in PBS (catalog No, DAGA-009H). Prior to use the AFB1-HRP solution was diluted to 600 ng/mL with PBS.

TABLE 1

Surfactant A Solution

| Component | Concentration in the PBS Solution |
| --- | --- |
| TWEEN 20 | 3 weight % |
| PVP360 | 3 weight % |
| PEG-6000 | 3 weight % |

The trigger solution for Example 1 was prepared as an aqueous solution of the components listed in Table 2.

TABLE 2

Trigger Solution Composition

| Component | Concentration in the Trigger Solution (g/L) |
| --- | --- |
| para-Coumaric acid | 1.31 |
| EDTA-dipotassium salt | 0.40 |
| TWEEN 20 | 2.00 |
| Hydrogen peroxide (30%) | 11.33 |
| Ethanol (200 proof) | 32.00 |
| Tris base | 1.33 |
| Tris hydrochloride | 2.22 |

Calculation
Equation 1:

Quotient Equation Fraction=Analyte Signal/[Glow Signal+Analyte Signal]

Example 1.

Dry feed corn was ground using a Romer Series II mill (Romer Labs, Newark, Del.) and passed through a #20 sieve. The sieved corn (10 g) was added to 50 mL of Surfactant B and mixed by shaking for 5 minutes. The supernatant from the sample was filtered through a 0.45 micron syringe filter (#F25029 polypropylene filter obtained from Thermo Fisher Scientific). The AFB1 stock sample (20 ppm in methanol described above) was diluted with the filtrate to prepare six test samples with AFB1 concentrations of 20 ppb, 5, ppb, 2.5 ppb, 1.25 ppb, 0.6 ppb, and 0.1 ppb (ppb=parts per billion). A corresponding series of six standard samples was prepared by diluting the AFB1 stock sample with Surfactant B. Three replicates were prepared at each AFB1 concentration.

For the competitive format assay, samples were prepared in microwell strips (catalog No. 70200756107, obtained from the 3M Company, Maplewood, Minn.) by first adding the AFB1 spiked samples (10 microliters) to the wells in the strip. Each well contained a single test sample or standard sample. Next, Surfactant A (30 microliters), AFB1-HRP solution (20 microliters), and sodium ascorbate solution (1 microliter of a 4 mM solution in PBS) were sequentially added to each well. The microwell strips were shaken for 10 seconds at 600 rpm with an IKA MS1 shaker (IKA Works Incorporated, Wilmington, Del.). The (anti-AFB1)-acridan solution (20 microliters) was then added to each well and the microwell strips were shaken for 5 minutes at 600 rpm.

A 3M MLS II injecting luminometer (available from the 3M Corporation) was used to add 80 microliters of trigger solution to each well. The instrument was set so that there was no time delay between the injection and luminescence signal measurement. Luminescence was measured in relative light units (RLU).

The initial analyte luminescence signal (flash signal) was measured by integrating for three seconds immediately after injection of the trigger solution.

The glow signal was measured by collecting one second integrations from time points 20 seconds to 300 seconds after injection of trigger solution. These RLU values were summed and scaled by a factor of 3/280 (0.0107) to adjust the glow integral signal to be the same order of magnitude as for the flash signal.

In Table 3, the mean Analyte Signal of the Test Sample (RLU) and the mean Analyte Signal of the Standard Sample (RLU) values are reported for each sample.

In Table 4, the mean Quotient Equation Fraction value (calculated from Equation 1) was calculated for each sample (test and standard samples). The values are reported in Table 3.

In Tables 5 and 6, the measured analyte (flash) signals and glow signals for each test and standard sample are reported

TABLE 3

| AFB1 Concentration in the Sample (ppb) | Mean Analyte Signal (RLU) of the Test Samples (n = 3) with Standard Deviation (SD) | Mean Analyte Signal (RLU) of the Standard Samples (n = 3) with Standard Deviation (SD) |
| --- | --- | --- |
| 20 | 1121 (SD = 103) | 1148 (SD = 81) |
| 5 | 1886 (SD = 210) | 2661 (SD = 229) |
| 2.5 | 3026 (SD = 410) | 3875 (SD = 342) |
| 1.25 | 3786 (SD = 362) | 5072 (SD = 532) |
| 0.6 | 4822 (SD = 296) | 6149 (SD = 328) |
| 0.1 | 5159 (SD = 219) | 6627 (SD = 123) |

TABLE 4

| AFB1 Concentration in the Sample (ppb) | Mean Quotient Equation Fraction for the Test Samples (n = 3) with Standard Deviation (SD) | Mean Quotient Equation Fraction for the Standard Samples (n = 3) with Standard Deviation (SD) |
| --- | --- | --- |
| 20 | 0.110 (SD = 0.009) | 0.096 (SD = 0.006) |
| 5 | 0.186 (SD = 0.021) | 0.221 (SD = 0.013) |
| 2.5 | 0.290 (SD = 0.042) | 0.331 (SD = 0.044) |
| 1.25 | 0.373 (SD = 0.051) | 0.425 (SD = 0.046) |
| 0.6 | 0.482 (SD = 0.033) | 0.511 (SD = 0.040) |
| 0.1 | 0.514 (SD = 0.020) | 0.562 (SD = 0.019) |

TABLE 5

| AFB1 Concentration in the Test Sample (ppb) | Analyte Signal (RLU) of the Test Sample | Glow Signal (RLU) of the Test Sample |
| --- | --- | --- |
| 20 | 977 | 8859 |
| 20 | 1174 | 9552 |
| 20 | 1212 | 8734 |
| 5 | 1602 | 8573 |
| 5 | 1951 | 7478 |
| 5 | 2105 | 8710 |
| 2.5 | 3089 | 7628 |
| 2.5 | 3495 | 6698 |
| 2.5 | 2495 | 7943 |
| 1.25 | 3453 | 6979 |
| 1.25 | 4289 | 5347 |
| 1.25 | 3617 | 6899 |
| 0.6 | 4670 | 5642 |
| 0.6 | 4559 | 5270 |
| 0.6 | 5236 | 4687 |
| 0.1 | 5280 | 5283 |
| 0.1 | 5345 | 4502 |
| 0.1 | 4852 | 4877 |

TABLE 6

| AFB1 Concentration in the Standard Sample (ppb) | Analyte Signal (RLU) of the Standard Sample | Glow Signal (RLU) of the Standard Sample |
| --- | --- | --- |
| 20 | 1111 | 10792 |
| 20 | 1260 | 10932 |
| 20 | 1072 | 10790 |
| 5 | 2504 | 9756 |
| 5 | 2985 | 9691 |
| 5 | 2494 | 8733 |
| 2.5 | 3957 | 7098 |
| 2.5 | 4247 | 7356 |
| 2.5 | 3421 | 9323 |
| 1.25 | 5421 | 6155 |
| 1.25 | 5476 | 6806 |
| 1.25 | 4320 | 7630 |
| 0.6 | 6258 | 6782 |
| 0.6 | 6485 | 4950 |
| 0.6 | 5704 | 6018 |
| 0.1 | 6788 | 5389 |
| 0.1 | 6602 | 4638 |
| 0.1 | 6490 | 5516 |

What is claimed is:

1. A method of assaying for an analyte in a sample, the method comprising
   forming a reaction mixture, and admixing a trigger solution to the reaction mixture; wherein
   the analyte to be assayed for may be present in the sample, the reaction mixture an aqueous solution comprising
      a chemiluminescent-labeled specific binding partner comprising a chemiluminescent label irreversibly bound to a first specific binding partner, the chemiluminescent-labeled specific bonding partner being capable of binding to the analyte to form an analyte-bound chemiluminescent labeled specific binding complex,
      an activator-labeled specific binding partner comprising an activator label irreversibly bound to a second specific binding partner, and
      a selective signal inhibiting agent; and wherein the method further comprises measuring an analyte signal,
   measuring a glow signal after measuring the analyte signal;
   measuring the analyte signal and the glow signal from a test sample containing an
   unknown quantity of the analyte; and
   preparing a calibration curve that compares the quotient of the analyte signal and the sum
   of the analyte signal and glow signal of the standard samples to the known concentration
   of analyte in the standard samples.

2. The method of claim 1, wherein the trigger solution further comprises an enhancer.

3. The method of claim 2, wherein the enhancer is one or more of phenol compounds, aromatic amines, benzoxazoles, hydroxybenzothiazoles, aryl boronic acids, or mixtures of any of the foregoing.

4. The method of claim 1, wherein the trigger solution further comprises an oxidation or reducing agent.

5. The method of claim 1, wherein the trigger solution further comprises a peroxide.

6. The method of claim 1, wherein the selective signal inhibiting agent is selected from the group consisting of ascorbic acid, isoascorbic acid, 6-hydroxy-2,5,7,8-tetramethylchroman-2-carboxylic acid, ascorbic acid 6-palmitate, 5,6-isopropylidiene-ascorbic acid, butylated hydroxy toluene, glutathione, uric acid, one or more tocopherols, and catechin.

7. The method of claim 1, wherein the activator label is a peroxidase enzyme.

8. The method of claim 1, wherein the chemiluminescent-labeled specific binding partner comprises a chemiluminescent label connected directly or indirectly to a specific binding partner, wherein the chemiluminescent label has formula

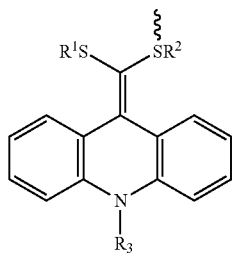

wherein
the wavy line designates the site of attachment to the specific binding partner or to a linker connecting the compound to the specific binding partner;
$R^1$ and $R^2$ are independently selected from the group consisting of substituted alkyl, unsubstituted alkyl, substituted alkyenyl, unsubstituted alkenyl, substituted alkynyl, unsubstituted alkynyl, substituted aralkyl, and unsubstituted aralkyl, wherein when $R^1$ or $R^2$ is substituted it is substituted with 1-3 substituents, each substituent independently selected from carbonyl, carboxyl, trialkylsilyl, —$SO_3$, glycosyl, —$PO_3$, halogen, hydroxyl, thiol, amino, $C(O)NHNH_2$, quaternary ammonium, and quaternary phosphonium;
$R^3$ is selected from the group consisting of substituted alkyl, unsubstituted alkyl, substituted alkyenyl, unsubstituted alkenyl, substituted alkynyl, unsubstituted alkynyl, substituted aralkyl, and unsubstituted aralkyl, wherein when $R^1$ or $R^2$ is substituted it is substituted with 1-3 substituents, each substituent independently selected from carbonyl, carboxyl, trialkylsilyl, —$SO_3$, glycosyl, —$PO_3$, halogen, hydroxyl, thiol, amino, $C(O)NHNH_2$, quaternary ammonium, and quaternary phosphonium.

9. The method of claim 1, wherein the chemiluminescent-labeled specific binding partner and the activator-labeled specific binding partner each bind to the analyte in the sample.

10. The method of claim 1, wherein the chemiluminescent-labeled specific binding partner comprises a chemiluminescent labeled compound connected to an analog of the analyte and further wherein the analyte and the chemiluminescent-labeled specific binding partner compete to bind with the activator-labeled specific binding partner.

11. The method of claim 1, wherein the unbound chemiluminescent label is selected from the group consisting of luminol, isoluminol, lophine, lucigenin and acridan, 2,3-dihydro-1,4-phthalazinedione, luciferin, dione, 3-(2'-spiroadamantane)-4-methoxy-4-(3''-phosphoryloxy)phenyl-1,2-dioxetane (AMPPD), 3-(2'-spiroadamantane)-4-methoxy-4-(3''-beta-D'-galactopyrano-yloxy)phenyl-1,2-dioxetane (AMPGD), disodium 3-(4-methoxyspiro {1,2-dioxetane-3, 2'-(5'-chloro)tricyclo [3.3.1.13,7]decan}-4-yl)phenyl phosphate, 1,2-dioxetanedione, and adamantylidene-adamantyl-1,2-dioxetane.

12. The method of claim 1, further comprising quantifying the amount of analyte in the test sample by comparing the quotient of the analyte signal and the sum of the analyte signal and glow signal from the test sample to a calibration curve.

13. The method of claim 1, wherein the analyte signal is a luminescence intensity or an area under the curve of a luminescence intensity, and further wherein the glow signal is a luminescence intensity or an area under the curve of a luminescence intensity.

* * * * *